United States Patent [19]

Turpen

[11] Patent Number: 4,942,017
[45] Date of Patent: Jul. 17, 1990

[54] RANDOM ACCESS CHEMISTRY ANALYZER

[75] Inventor: Jon D. Turpen, Jackson, N.J.

[73] Assignee: Turpen Laboratory Systems, Inc., Lakewood, N.J.

[21] Appl. No.: 125,216

[22] Filed: Nov. 25, 1987

Related U.S. Application Data

[62] Division of Ser. No. 801,052, Nov. 22, 1985.

[51] Int. Cl.⁵ .......................................... G01N 35/00
[52] U.S. Cl. ........................................ 422/64; 422/63; 422/99; 422/102
[58] Field of Search .................... 422/63-67, 422/72, 99, 102

[56] References Cited

U.S. PATENT DOCUMENTS

| | | | |
|---|---|---|---|
| 3,545,864 | 12/1970 | Dibbern | 422/68 |
| 4,256,696 | 3/1981 | Soodak | 422/64 |
| 4,309,384 | 1/1982 | Trod | 422/72 |
| 4,558,946 | 12/1985 | Galle et al. | 422/102 |
| 4,762,413 | 8/1988 | Namba | 422/64 |
| 4,774,057 | 9/1988 | Uffenheimer | 422/72 |

Primary Examiner—Robert J. Warden
Assistant Examiner—D. John Griffith, Jr.
Attorney, Agent, or Firm—John N. Bain; Raymond J. Lillie

[57] ABSTRACT

The ability to provide a random assortment of chemical analyses is provided by an improved photometric analyzer system. The analyzer has a rotary sample holding means which periodically indexes to place a different cuvette in the optical path of the photometer. An improved cuvette is provided which permits preloading of the samples and reagents without mixing.

7 Claims, 3 Drawing Sheets

RANDOM ACCESS CHEMISTRY ANALYZER

This is a division, of application Ser. No. 801,052, filed November 22, 1985.

BACKGROUND OF THE INVENTION

1. Field of the Invention

This invention relates to photometric chemical analyzers. More particularly, this invention relates to an improved photometric analyzer capable of performing kinetic rate measurements of enzyme activity, end-point determinations of metabolites, and fixed-time substrate analyses.

2. Description of the Prior Art

The measurement of absorbance of light is an important method of analyzing the chemical composition of fluids. This type of measurement is usually performed by passing a narrow bandwidth spectrum of visible light through the fluid under test and measuring the amount of light absorbed by the fluid. The degree of absorption is proportional to the concentration of the chemical component or components which will absorb the particular spectrum being applied. By providing the capability of directing spectra of several different wavelengths or colors through the fluid, one may conduct a fairly complete analysis.

The fluid or fluids under consideration are placed in specialized test tubes called cuvettes. The cuvette typically has a square or rectangular cross-section where at least two opposing sides are prefectly or nearly perfectly parallel. The parallel relationship is important for minimizing diffraction of a visible light beam as it passes through the cuvette.

In one known arrangement of a chemical analyzer, several cuvettes are placed together in a line on a platform. A light source is arranged to be passed through each cuvette serially by moving either the light source or the row of cuvettes. A detector is placed on the other side of the cuvettes, in line with the optical path of the light beam emanating from the light source. Finally, a filter which permits only a narrow bandwidth spectrum of visible light to pass is placed in the optical path of the light source between the source and the cuvettes. One cuvette may be left empty to serve as the reference standard.

With the arrangement described immediately above, one is limited to performing a single test on the cuvettes in a batch mode. If one wishes to perform another test on the fluids, a second batch of cuvettes must be assembled.

OBJECTS OF THE INVENTION

It is an object of the invention to provide a chemical analyzer capable of performing more than one analysis on a single group of test samples.

It is a further object of the invention to provide a chemical analyzer capable of performing tests in batch, random access, and profile modes.

It is a further object of the invention to provide a chemical analyzer which is programmable.

It is a further object of the invention to provide an improved cuvette for use with the analyzer according to the invention.

SUMMARY OF THE INVENTION

These objects as well as others not enumerated here are achieved by the invention, one embodiment of which may include a rotatable sample holding means having at least two sample retaining means, a light source, a narrow bandwidth filter, and a light detector. These components are arranged such that the filter and the rotatable sample holder are located in the optical path of the light generated by the light sourcre. Thus, in one configuration, the light leaves the light source, passes through the filter the sample retaining means, and is ultimately received by the light detector. The output of the light detector is provided to a computer for calculation of the degree of absorbance.

A further feature of the invention is an improved cuvette having an integral reservoir for the reagent. In an alternative embodiment, the cuvette is provided with a detachable reservoir.

BRIEF DESCRIPTION OF THE DRAWINGS

A more complete understanding of the present invention, as well as other objects and advantages thereof not enumerated, will become apparent upon consideration of the following detailed description, especially when considered in light of the accompanying drawings wherein.

DETAILED DESCRIPTION OF THE INVENTION

Figure 1:
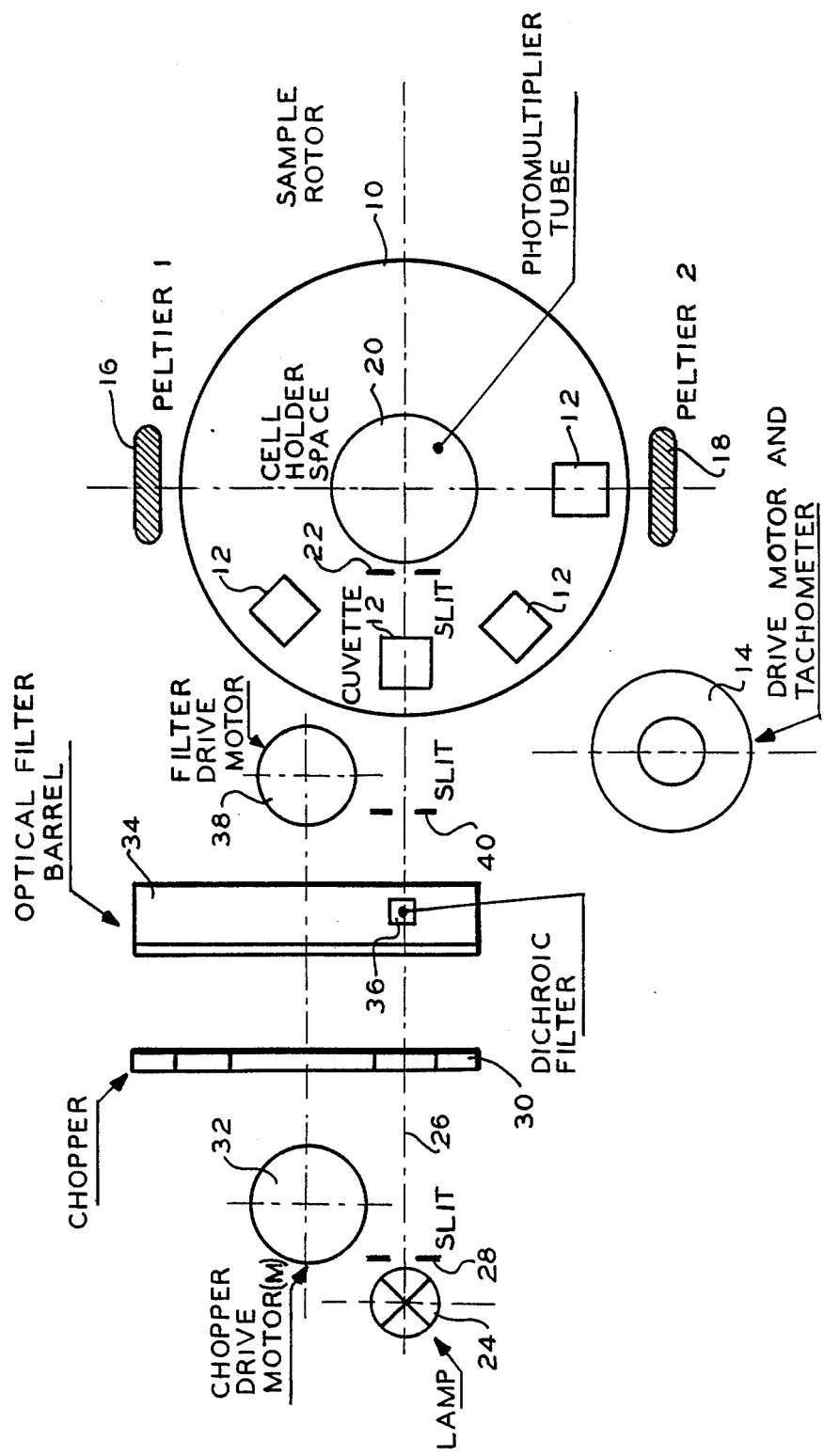
FIG. 1 is schematic diagram of the invention.

The structure and operation of the chemical analyzer can be best explained by reference to FIG. 1. The sample rotor 10 provides a rotating platform for the cuvettes 12 which contain the fluids under test. The sample rotor 10 is driven by the drive motor and tachometer 14. On the periphery of the sample rotor 10 are two Peltier units 16 and 18 for maintaining the desired temperature level of the samples in the cuvettes 12. At the center of the sample rotor 10 is a photomultiplier tube 20, which serves to detect unabsorbed light passing through the cuvette 12, as will be explained later. Finally, there is a detector optical slit 22 positioned adjacent to the photomultiplier tube 20.

In order to conduct the photometric analysis, it is necessary to generate light. This is done by the light source or lamp 24. The imaginary line intersecting the lamp 24 and the photomultiplier tube 20, designated by reference numeral 26, represents the optical path of the chemical analyzer system.

A second optical slit 28 is positioned in the optical path 26 adjacent the lamp 24. Following the optical slit 28 is a chopper 30 which is driven by the chopper drive motor 32. The next element along the optical path 26 is the optical filter barrel 34, which contains several narrow bandwidth interference filter elements 36. The filter drive motor 38 turns the optical filter barrel 34, positioning it at the desired narrow bandwidth interference filter element 36. The remaining component in the optical path 26 is a third optical slit 40 positioned between the optical filter barrel 34 and the sample rotor 10.

Figure 2:
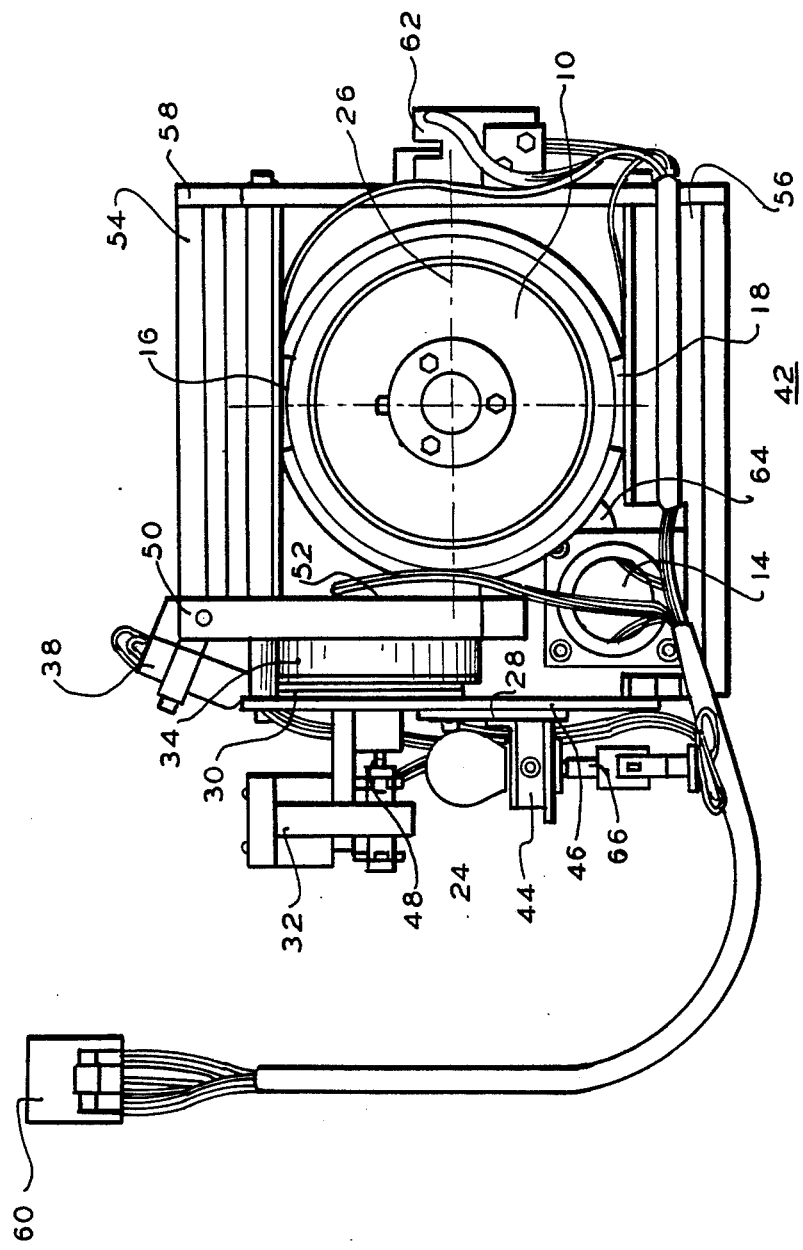
FIG. 2 is a detailed top view of the invention.

Referring now to FIG. 2, the optical/rotor unit according to the present invention is disclosed in a top view and designated generally by the reference numeral 42. Several of the elements discussed in connection with FIG. 1 can be seen in FIG. 2. For instance, at the approximate center of the optical/rotor unit 42 is the sample rotor 10. At its periphery are Peltier units 16 and 18. To the lower left of the sample rotor 10 is the rotor drive motor and tachometer 14. Lamp 24 is supported by a lamp-holding bracket 44. Approximately adjacent to the lamp 24 is the optical slit 28 which is attached to a left outer frame member 46. The chopper drive motor 32 is also attached to the left outer frame member 46. A chopper drive shaft 48 extends through the left outer frame number 46 to the chopper 30 which is rigidly fixed to the shaft the 48. Immediately adjacent to the chopper 30 is the optical filter barrel 34. The optical filter barrel 34 is driven and positioned by the filter drive 38 which is affixed to an inner frame member 50. The actual position of the optical filter barrel 34 is detected through a filter barrel potentiometer 52, which is mounted on the inner frame member 50 and provides rotational support for the optical filter barrel 34.

The Peltier units 16 and 18 are provided with heat sinks 54 and 56, respectively. Heat sink 54 is attached to the inner frame member 50 on one side and to a right outer frame member 58 on the other side. Heat sink 56 spans between the left outer frame member 46 and the right outer frame member 58.

Power for the lamp 24, the chopper drive motor 32, the filter barrel drive 38, and the sample rotor drive motor 14, as well as the input and output for the photomultiplier tube 20 is provided by a cable and connector assembly 60 which is partially terminated at an optical sensor printed circuit board 62. Finally, mechanical drive power from the sample rotor drive motor 14 is provided to the sample rotor 10 through an idle gear 64. The cable and connector assembly 60 is also partially terminated at a lamp connector 66 which attaches to the lamp 24 at the lamp-holding bracket 44. Other terminations are at the chopper drive motor 32, the filter barrel potentiometer 52, Peltier units 16 and 18, and the rotor drive motor and tachometer 14.

Figure 3:
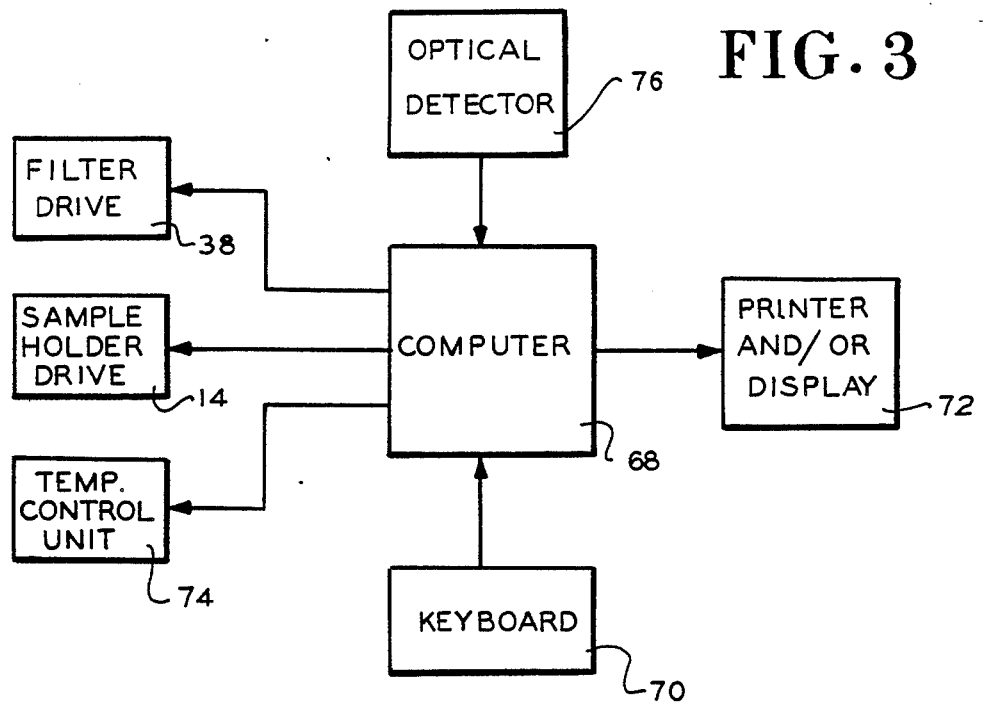
FIG. 3 is a block schematic diagram of the control system for the invention.

The output of the photomultiplier tube 20 is connected to the optical sensor printed circuit board 62, the output of which is provided to a computer. The interconnections between the chemical analyzer and the computer can be best explained by referring to FIG. 3. Communication to and from the computer 68 by the oprator is achieved through a keyboard 70 and an output peripheral such as a printer of display 72. In accordance with instructions stored in the memory of the computer 68, positioning commands are provided to the filter barrel drive 38 and the rotor drive 14. The computer also provides signals to the Peltier units through temperature control unit 74. Finally, test data is derived from the optical/rotor unit 42 from the output of the photomultiplier tube 20 (FIG. 1) which is processed through the optical detector 76, which partially comprises the optical sensor printed circuit board 62. This signal in turn is sent to the computer 68 for processing in accordance with instructions in memory, ultimately yielding the test results.

A wide variety of tests may be performed with the invention using procedures well knonw in the art. Computer control offers the flexibility of providing testing capability in batch, random access, and profile modes.

Figure 4:
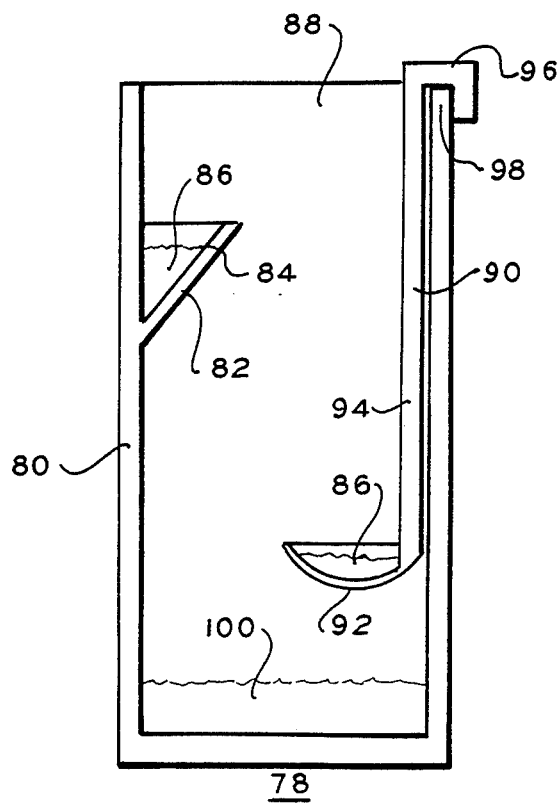
FIG. 4 is a cross-sectional diagram of the cuvette according to the invention.

The design of the cuvette can be best described by reference to FIG. 4, which illustrates the cuvette 78 in cross-section. As is standard with cuvettes, the cuvette 78 has at least two opposing walls which are parallel with respect to each other. This is most easily achieved with a structure having a square or rectangular cross-section. Two arrangements for storing the sample or reagent prior to mixing are provided. The first, integral with the wall 80 of the cuvette 78, is a reservoir 82 having an inwardly slanting wall 84. With this configuration, the sample or reagent 86 is added directly through the opening or mouth 88 of the cuvette 78. The other component 100 is placed in the bottom of the curvette 78.

In an alternative arrangement, a spoon assembly 90 clips on the cuvette 78. The spoon assembly 90 has a spoon 92 which is attached to a handle 94. At the other end of the handle 94 is a hook 96 which slips over the edge 98 of the wall 80 of the cuvette 78. As with the integral reservoir configuration, the reagent or sample 86 is deposited in the spoon 92 and the second component 100 is placed in the bottom of the cuvette 78.

Just prior to commencing a test, the samples or fluids in the cuvettes 78 are mixed. This may be done off-line, or on-line in the photometer unit, using well known apparatus. To mix the samples, vibration can be imparted to the cuvettes 78, creating a vortex. By using cuvettes having sample holding reservoirs, one can preload the samples or reagents into a series of cuvettes, mix the chemical components, and have all reactions commence simultaneously. This will reduce error due to non-uniform starting times for cuvette reactions.

While there has been described what is believed to be the preferred embodiment of the invention, those skilled in the art will recognize that other and further modifications may be made thereto without departing from the spirit of the invention, and it is intended to claim all such embodiments that fall within the true scope of the invention.

What is claimed:

1. A chemical analyzer system, comprising:
   rotatable sample holding means having at least two cuvette means, each of said at least two cuvette means including a sample or reagent holding means, said sample or reagent holding means being a detachably removable spoon, said spoon having a detachably removable attachment means;
   light source means;
   filter means; and
   light detection means, said light detection means including a photomultiplier tube, wherein said filter means and said rotable sample holding means are in the optical path of the light generated by said light source means and wherein said light detection means is at the end of said optical path.

2. A chemical analyzer system as set forth in claim 1 above where said filter means comprises at least one narrow bandwidth interference filter.

3. A chemical analyzer system as set forth in claim 1 above where said detachably removable attachment is a handle extending upwardly from said spoon.

4. A chemical analyzer system, as set forth in claim 1 above, further comprising chopper means positioned in said optical path between said light source means and said filter means.

5. A chemical analyzer system as set forth in claim 4 above, further comprising light source slit means positioned in said optical path adjacent said light source means, filter slit means positioned in said optical path between said filter means and said rotatable sample holding means, and light detection slit means positioned in said optical path adjacent said light detection means.

6. A chemical analyzer system as set forth in claim 1 above where said rotatable sample holding means includes heat source means.

7. A chemical analyzer system as set forth in claim 6 above where said heat source means includes at least one Peltier means.

* * * * *